US00PP13248P3

(12) United States Plant Patent
Utecht

(10) Patent No.: US PP13,248 P3
(45) Date of Patent: Nov. 19, 2002

(54) GERANIUM PLANT NAMED 'FISTON'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,635

(22) Filed: Nov. 26, 2001

(65) Prior Publication Data

US 2002/0088040 P1 Jul. 4, 2002

(51) Int. Cl.[7] ..... A01H 5/00

(52) U.S. Cl. ..... Plt./330

(58) Field of Search ..... Plt./330

*Primary Examiner*—Kent L. Bell
(74) *Attorney, Agent, or Firm*—Foley & Lardner

(57) ABSTRACT

A new and distinct cultivar of geranium plant named 'Fiston', as described and illustrated, and particularly characterized by the combined features of bright coral, round flowers, medium to large umbels on relatively short peduncles, medium green leaves with slight zonation, and medium sized, but relatively low and tight plant habit.

1 Drawing Sheet

BOTANICAL CLASSIFICATION

*Pelargonium zonale.*

VARIETY DENOMINATION

'Fiston'.

BACKGROUND OF THE INVENTION

The present invention comprises a new and distinct cultivar of geranium, botanically known as *Pelargonium zonale*, and hereinafter referred to by the cultivar name 'Fiston'.

'Fiston' is a product of a planned breeding program which had the objective of creating new geranium varieties with deep salmon colored, semi-double flowers, and medium sized to moderately tall plant habit.

'Fiston' originated from a hybridization made by the inventor Angelika Utecht in a controlled breeding program in Galdar, Gran Canaria, Spain, in 1996. The female parent was an unpatented hybrid seedling, no. K91-1216-3, having uniformly salmon colored, single-type flowers, medium green foliage with strong zonation, and vigorous growth. The male parent of 'Fiston' was the patented variety 'Fiseye' (U.S. Plant Pat. No. 11,302), which is characterized by light violet, weakly semi-double flowers with red eyes, relatively short peduncles, uniform green foliage, and medium sized plant habit.

'Fiston' was selected as one flowering plant within the progeny of the stated cross by Angelika Utecht in 1997, in a controlled environment in Galdar, Gran Canaria, Spain. The first act of asexual reproduction of 'Fiston' was accomplished when vegetative cuttings were taken from the initial selection in the fall of 1997, in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fiston' are firmly fixed and are retained through successive generations of asexual reproduction. The new cultivar reproduces true to type.

'Fiston' has not been observed under all possible environmental conditions. The phenotype may vary significantly with variations in environment such as temperature, light intensity and day length. The following observations, measurements, and comparisons describe plants grown in Hillsheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fiston' in combination distinguish this geranium as a new and distinct cultivar:

1. round, bright coral colored flowers;
2. medium to large, semi-spherically shaped umbels, not very high above the foliage;
3. relatively large, grass-green foliage with slight zonation;
4. moderately compact growth, and medium sized, but relatively low plant habit; and
5. early to medium spring flowering response.

Of the many commercial cultivars known to the present inventor, the most similar in comparison to 'Fiston' are the patented variety 'Americana Coral' (U.S. Plant Pat. No. 7,934), and the related cultivar 'Fissalmrose', (U.S. Plant Pat. No. 12,496).

In comparison to 'Americana Coral', 'Fiston' has a somewhat more rose, less orange hue of flower color, somewhat smaller umbels, shorter peduncles, and more compact plant habit. In comparison to 'Fissalmrose', 'Fiston' has a more intense flower color, only very weak zonation on leaves, and distinctly lower and generally more compact plant habit.

BRIEF DESCRIPTION OF THE DRAWING

The accompanying photographic drawing shows typical flower and foliage characteristics of 'Fiston' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants developed in a greenhouse in May 2001, in Hillscheid, Germany. The measurements were taken in Langley, British Columbia, Canada, in early July, 2001, 8 weeks after planting of rooted cuttings. The plants were growing in 8 inch containers, they had not been pinched.

Inflorescence:
- *Type.*—Umbel.
- *Shape.*—Semi-spherical.
- *Average diameter.*—113 mm.
- *Average depth.*—60 mm.
- *Peduncle length.*—170 mm.
- *Peduncle color.*—Light green, RHS 143A to RHS 144A, no anthocyanin.
- *Pedicel length.*—28 mm.
- *Pedicel color.*—Light green, RHS 143 C, upper end slightly reddish, RHS 179 A.
- *Number of flowers per umbel.*—About 25–35.

Corolla:
- *Average diameter.*—50 mm.
- *Form.*—Semi-double.
- *Shape.*—Round outline, cup-shaped, often with a narrow gap between upper and lower petals.
- *Number of petals.*—Average 9.4.
- *Number of petaloids.*—1–2, narrow, colored like petals.
- *Shape of petals.*—Obovate, base attenuate, upper end is rounded, margin is entire, or occasionally slightly serrulated at the apex.
- *Size of petals.*—Upper petals length 24–26 mm, width 22–23 mm; lower petals length 23–25 mm; width 25 mm.
- *Color (general tonality from a distance of three meters).*—Light coral.
- *Color of upper petals.*—Between RHS 50 A and RHS 52 A.
- *Markings of upper petals.*—Small pink eye, RHS 67 C.
- *Color of lower petals.*—RHS 52 A.
- *Markings of lower petals.*—Absent.
- *Color of lower surface of petals.*—Mainly light red RHS 46 D, white near bases, RHS 155 D.
- *Color of sepals.*—Outer surface light green, RHS 143 C, near base very weak brown RHS 179 A; inner surface light green, RHS 143 C, near base 179 B.
- *Number of sepals.*—Usually 5.
- *Shape of sepals.*—Linear to lanceolate, acute tip, truncate base, surface with very short pubescence, margin entire.
- *Size of sepals.*—11–13 mm long, 4 mm wide for the largest upper sepal, 2–3 mm in width for the other sepals.

Bud (just before petals unfold):
- *Shape.*—Elliptical.
- *Color (sepals).*—Light green, RHS 143 C.
- *Color (petals).*—Pink, RHS 52 B, and white, RHS 155 D, marbled.
- *Length.*—16 mm.
- *Width.*—10 mm.

Reproductive organs:
- *Androecium.*—About 5 fertile anthers, filaments white, RHS 155 D, moderate pollen, orange, RHS 30 A.
- *Gynoecium.*—One pistil, style and stigma pink, RHS 52 B, 5 to 6 lobed stigma.
- *Fertility/seed set.*—Occasionally a few seeds are developed. Fruit: oblong, about 6 mm in diameter, with rostrum (beak), total length about 42 mm. Seed: Oblong, 4–5 mm long, brown, RHS 177 B.

Spring flowering response period: In Hillscheid, Germany, in 2000 plants had on average 1.4 flowers opened 8 weeks after planting of rooted cuttings.

Outdoor flower production: Continuously flowering, the flower count in 2000 in Hillscheid, Germany, indicated about 2.3 inflorescences per plant in mid May.

Durability: Good stability of flower color, good rain resistance.

Lastingness of the individual flower: About 8 days at 18° C., about 18 days for the umbel.

Pest/disease resistance/susceptibility: No observations to date.

Fragrance: None.

PLANT

Foliage:
- *Shape.*—Kidney-shaped, with cordate base, weak to medium lobes, at the base open.
- *Margin.*—Bicrenated.
- *Texture.*—Upper surface smooth, velvety.
- *Size of leaf.*—89 mm wide, 53 mm long.
- *Color of upper surface.*—Medium green, approximately RHS 137 C to RHS 137 D.
- *Color of zonation.*—Green, about RHS 147 A, weak may not be visible on mature leaves during the summer.
- *Color of lower surface.*—RHS 137 D.
- *Petioles.*—60–70 mm long, 3 mm diameter, light green in color, approximately RHS 143 C to RHS 144 C.

General appearance and form:
- *Stem color.*—Green, RHS 144 B to RHS 144 D.
- *Internode length.*—10–15 mm.
- *Branching pattern.*—7.8 branches.
- *Size of plants.*—Height 21.6 cm, width 38.4 cm, as measured from the top of the soil (base of the main stem) to the surface of the foliage canopy, without inflorescences.

I claim:

1. A new and distinct cultivar of geranium plant named 'Fiston', as described and illustrated herein.

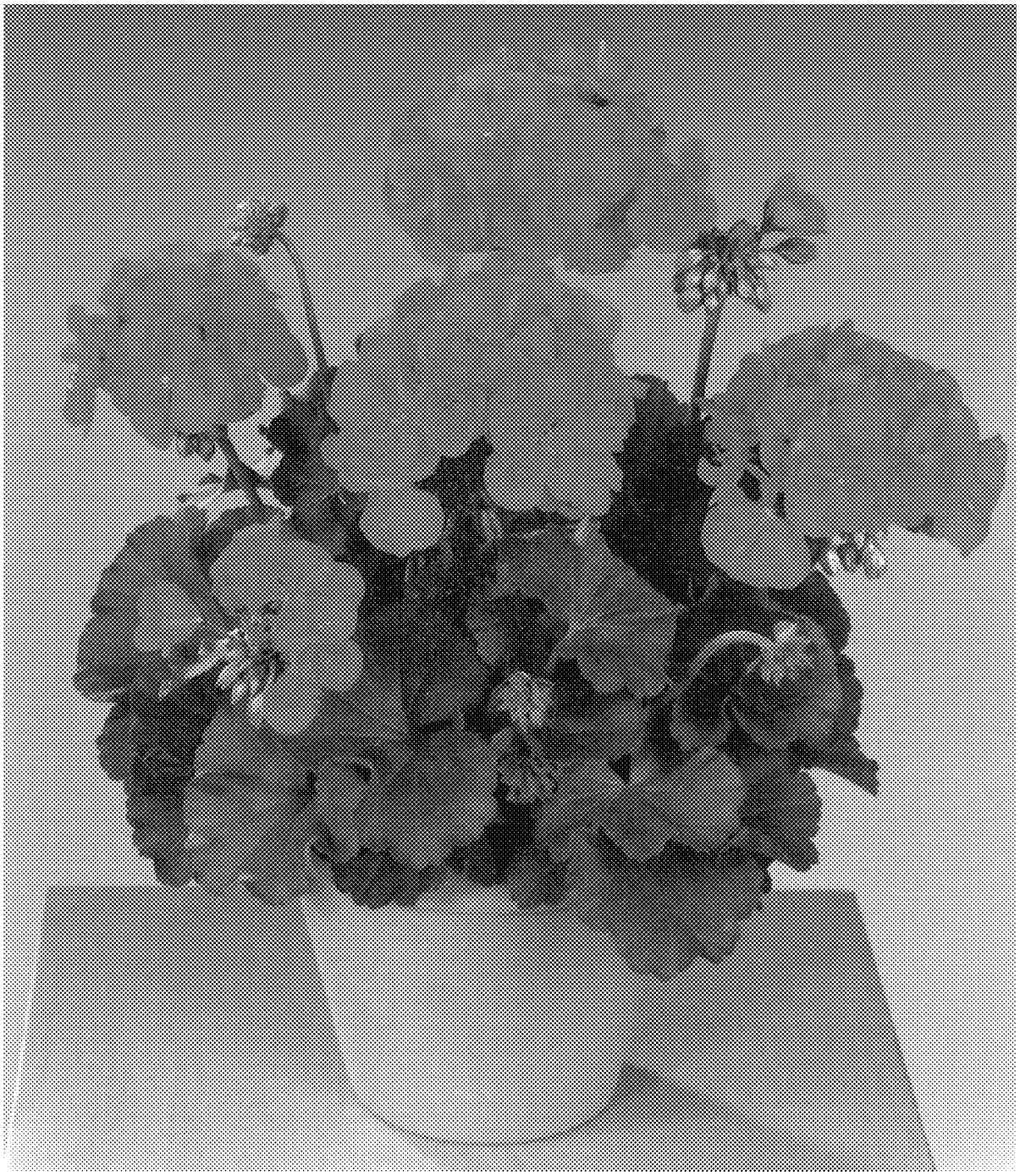

* * * * *